United States Patent
Kocaoglu et al.

(10) Patent No.: US 8,974,059 B2
(45) Date of Patent: Mar. 10, 2015

(54) RETINAL IMAGING SYSTEM FOR THE MOUSE OR RAT OR OTHER SMALL ANIMALS

(75) Inventors: Omer Kocaoglu, Miami, FL (US);
Stephen Uhlhorn, Palm Beach Gradens, FL (US); Eleut Hernandez, Miami Beach, FL (US); Vittorio Porciatti, Miami, FL (US); Jean-Marie Parel, Miami Shores, FL (US); Fabrice Manns, Palmetto Bay, FL (US)

(73) Assignee: University of Miami, Miami, FL (US)

( * ) Notice: Subject to any disclaimer, the term of this patent is extended or adjusted under 35 U.S.C. 154(b) by 481 days.

(21) Appl. No.: 13/132,748

(22) PCT Filed: Dec. 2, 2009

(86) PCT No.: PCT/US2009/066325
§ 371 (c)(1),
(2), (4) Date: Jun. 3, 2011

(87) PCT Pub. No.: WO2010/065581
PCT Pub. Date: Jun. 10, 2010

(65) Prior Publication Data
US 2011/0234976 A1 Sep. 29, 2011

Related U.S. Application Data

(60) Provisional application No. 61/119,571, filed on Dec. 3, 2008.

(51) Int. Cl.
*A61B 3/14* (2006.01)
*A61B 3/10* (2006.01)
*A61B 19/00* (2006.01)
*A61F 9/008* (2006.01)

(52) U.S. Cl.
CPC ......... *A61B 3/102* (2013.01); *A61B 2019/5234* (2013.01); *A61F 9/008* (2013.01); *A61F 2009/00863* (2013.01)
USPC .......................................... 351/206; 351/221

(58) Field of Classification Search
USPC ......... 351/200, 203, 205, 221, 222, 243, 245, 351/246, 206
See application file for complete search history.

(56) References Cited

U.S. PATENT DOCUMENTS

| | | | |
|---|---|---|---|
| 6,741,359 B2 * | 5/2004 | Wei et al. | 356/512 |
| 7,140,730 B2 | 11/2006 | Wei et al. | |
| 7,227,646 B2 | 6/2007 | Tanno et al. | |
| 7,301,644 B2 | 11/2007 | Knighton et al. | |
| 7,828,437 B2 * | 11/2010 | Kikawa et al. | 351/206 |
| 2007/0171363 A1 * | 7/2007 | Chen et al. | 351/200 |

OTHER PUBLICATIONS

International Search Report and Written Opinion dated Jun. 24, 2010 for the International Application No. PCT/US09/066325, International Filing Date Dec. 2, 2009 (consisting of 10 pages).

* cited by examiner

*Primary Examiner* — Scott J Sugarman
*Assistant Examiner* — Brandi Thomas
(74) *Attorney, Agent, or Firm* — Christopher & Weisberg, P.A.

(57) ABSTRACT

A small animal imaging system comprising a base element and a camera coupled to the base element, the camera being sized to image the eye of a small animal. A light-emitting diode is also included coupled to the base element. An OCT imaging apparatus is also included coupled to the base element. An X-Y scanner is also included coupled to the base element in communication with the OCT imaging apparatus.

11 Claims, 5 Drawing Sheets

| Color | Target Tissue | Mechanism |
|---|---|---|
| Red | Choroid | Deep penetration, low scattering, absorbed by hemoglobin. |
| Blue | Nerve Fibers | Strong scattering, scattering by NFL. |
| Green | Blood Vessels | Strong absorption by hemoglobin. |
| White | All | Combination of the effects of red, blue, and green wavelengths |
| Warm White | All | Combination of the effects of red, blue, and green wavelengths |

*FIG. 6*

RETINAL IMAGING SYSTEM FOR THE MOUSE OR RAT OR OTHER SMALL ANIMALS

CROSS-REFERENCE TO RELATED APPLICATION

This application is a U.S. National Stage application of International Application No. PCT/US2009/066325, filed Dec. 2,2009, entitled RENTINAL IMAGING SYSTEM FOR THE MOUSE OR RAT OR OTHER SMALL ANIMALS, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for acquiring fundus and Optical Coherence Tomography (OCT) retinal or corneal images of mice, or other small animals, during examination or screening.

BACKGROUND OF THE INVENTION

Mice have become the primary model for the study of ocular diseases in humans. Because mice and humans share about 95% of their genome, a given gene in a mouse will likely have a homologous chromosomal segment in humans. Moreover, using mice for genetic research is advantageous because, for example, genetically identical mice can be inbred, disease progression in mice is more rapid due to their short life span, and mice are readily available for examination. Because of these advantages, mouse models are expected to play a vital role in the development of new pharmaceutical therapies for glaucoma, retinal degeneration, and retinal vascular diseases.

In vivo quantitative and qualitative assessment of retinal morphology and anatomy in mice, is a necessary fundamental step to characterize the various ocular disease phenotypes, track disease progression, or evaluated disease therapies. Traditional approaches to imaging the interior portion of the mouse eye, known as the fundus, have proven to be tedious. One commercial technique of imaging the mouse eye relied upon a blind technique, wherein the operator fired a small camera multiple times at the mouse eye, without being able to see the image or assurance that a clear image was produced. Another alternative was to use two operators, one to hold the mouse and another to operate the camera, but this technique often produced inferior quality images.

Presently, optical coherence tomography (OCT) is a recognized technique for rapid real-time evaluation of retinal morphology in live mouse. OCT can provide a high-resolution, cross-sectional image of the retinal microstructure. However, there are several challenges with OCT in accurately and effectively imaging the interior surface of the fundus. For example, the length of a mouse eye is approximately ⅛ the size of a human eye, making image capture more difficult. Additionally, mice do not voluntarily agree to be fixated for a retinal examination, making it difficult to align the imaging device to the precise ocular position. Moreover, the eye of a mouse dehydrates very rapidly, requiring researchers to make rapid image acquisitions.

One solution to the alignment problem presented by mouse OCT imaging is to obtain a real-time image of the mouse eye and fundus, which would make it possible to visualize to the OCT area of analysis to control the OCT scan position. Accordingly, several techniques have been developed to acquire fundus images of the mouse eye, such as using a small animal fundus camera with a lens, or using human fundus camera or a slit-lamp with a lens.

Slit-lamps combined with OCT imaging have been shown to produce fast and reliable images of the mouse fundus. Slit-lamp bio-microscopes provide a flexible design platform suitable for many varieties of small animals. However, slit-lamps themselves are often large, complex, and difficult to align for small animals. Moreover, slit-lamps traditionally employ an incandescent white light source to illuminate the fundus, which are often large and require a high current to operate. As such, a need exists for a compact table-top combined fundus camera and OCT imaging system for live mice that records and images rapidly and accurately.

SUMMARY OF THE INVENTION

The present invention advantageously provides for a small animal imaging system. The system includes a base element and a camera coupled to the base element the camera being sized to image the eye of a small animal. A light-emitting diode is also included and coupled to the base element. An OCT imaging apparatus is also included coupled to the base element. An X-Y scanner is also included coupled to the base element in communication with the OCT imaging apparatus.

In another embodiment, the method includes providing an OCT imaging apparatus and a camera sized to image the fundus of a small animal. The camera is optically aligned with the fundus of a small animal. A desired area of the fundus is then visualized for OCT imaging. The desired area of the fundus is then illuminated with light from a light-emitting diode. An image of the desired area of the fundus is then acquired with the camera and then an OCT image is acquired of the desired area.

In yet another embodiment, the system includes a base element and a camera coupled to the base element, the camera being sized to image the eye of a small animal. An OCT imaging apparatus is included and coupled to the base element. A light-emitting diode is included and also coupled to the base element. A first illumination lens is also included coupled to the base element proximate the light-emitting diode. A reflection mirror coupled to the base element is included proximate the first illumination lens, the reflection mirror defining an aperture approximately at its center. A second illumination lens is also included coupled to the base element, the second illumination lens being oriented such that a longitudinal axis defined by the second illumination lens is substantially parallel to a longitudinal axis defined by the first illumination lens. A first folding mirror is also included coupled to the base element, the first folding mirror being oriented such that a longitudinal axis defined by the first folding mirror is substantially parallel to a longitudinal axis defined by the reflection mirror. A second folding mirror is also included coupled to the base element, the second folding mirror being oriented such that a longitudinal axis defined by the second folding mirror is substantially perpendicular to the longitudinal axis defined by the first folding mirror. A hot mirror is also included coupled to the base element, the hot mirror allowing light emitted by the light-emitting diode to pass through the hot mirror, the hot mirror also reflecting infrared wavelengths of light generated by the OCT imaging apparatus. A scanning lens coupled to the base element is also included, the scanning lens being disposed between the second folding mirror and the hot mirror. An auxiliary lens is also included coupled to the base element. A collimating lens is also included coupled to the base element proximate the OCT imaging apparatus. An X-Y scanner is also included coupled to the base element, the X-Y scanner being in communication with the OCT imaging apparatus.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
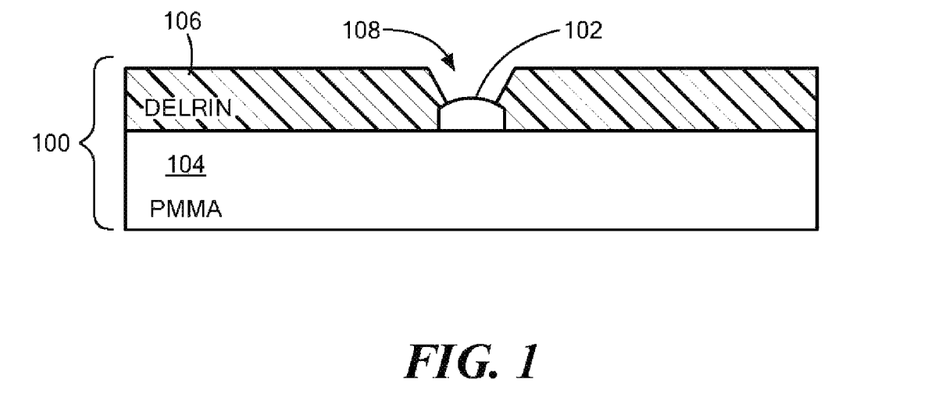
FIG. 1 is a longitudinal cross-sectional view of a model mouse eye calibration device.

Referring now to the figures in which like reference designators refer to like elements, there is shown in FIG. 1 a cross-sectional view of a model mouse eye used to calibrate an OCT imaging system in accordance with the principles of the present invention referred to generally as "100." The model eye 100 may comprise a plano-convex lens 102 with an optical power matching the optical power of the mouse eye (approximately 560 D). The plano-convex lens 102 may be approximately 2.5 mm in diameter. The model eye 100 may further include a Polymethyl methacrylate (PMMA) disc 104, or other similar material, placed in contact with the posterior surface of the plano-convex lens 102. The PMMA disc 104 may be approximately 25.4 mm in length, or any length, and have a height of approximately 3.72 mm, or any height. The posterior surface of the PMMA disc 104 may be located coincident with the focal plane of the plano-convex lens 102. A black, or similarly colored disc 106, for example Delrin, may also be included. The disc 106 may be glued or otherwise affixed to the PMMA disc 104 to simulate the iris and pupil of the mouse eye. The disc 106 may further aid in fixing the plano-convex lens 102 to the PMMA disc 104. The disc 106 may be sized to have approximately the same length as the PMMA disc 104. The disc 106 may define an opening 108, which may be defined at approximately the center of disc 106 and may be substantially trapezoidal in shape. In an embodiment, the opening 108 is has a length of 3.2 mm at its longest point. For example, as shown in FIG. 1, the opening 108 may be sized such that a portion of the opening 108 proximate the plano-convex lens 102 is smaller than a portion of the opening 108 distal the plano-convex lens 102. The model eye 100 may further include millimetric paper taped on the posterior surface to quantify the field of view.

Figure 2:
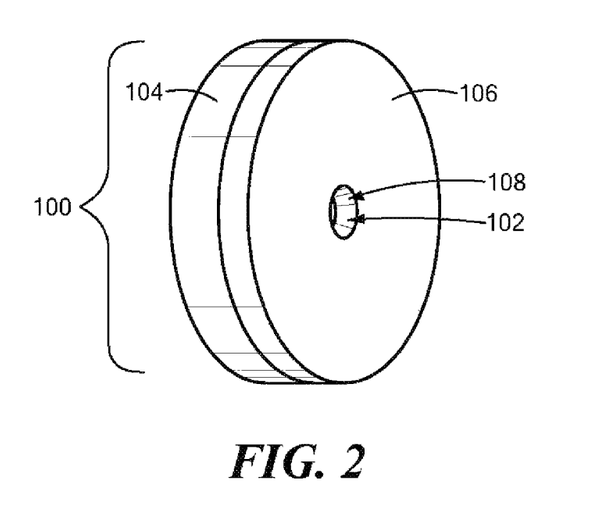
FIG. 2 is a perspective view of the model mouse eye calibration device of FIG. 1.

Referring now to FIG. 2, showing the model eye 100 which includes the plano-convex lens 102, the PMMA disc 104, and the disc 106. In this embodiment, the model eye 100 may visually and characteristically resemble the eye of a small animal such as a rat or mouse. The terms "small animal" referred to herein define animals of similar size and dimensions to that of a mouse or rat. The model eye 100 may be utilized to calibrate various imaging systems that image the fundus of a small animal's eye. For example, the model eye 100 may be used to focus an OCT imaging system or to identify a target area on the fundus to be examined. Once the target area on the model eye 100 is identified, a mouse or other small animal may substitute for the model eye 100 and be imaged accordingly. The model eye 100 may allow for faster and more accurate examination of the fundus of a small animal as calibration times may be reduced and accuracy may be increased.

The model eye 100 may further be adaptable to model any size eye of a small animal. For example, a rat and mouse may have differently sized eyes, and in particular, lenses. To calibrate the desired imaging system, the plano-convex lens 102 and disc 106 may be removable coupled the PMMA disc 104, such that a differently size plano-convex lens 102 and disc 106 defining a desired size opening 108 may be used as needed.

Figure 3:
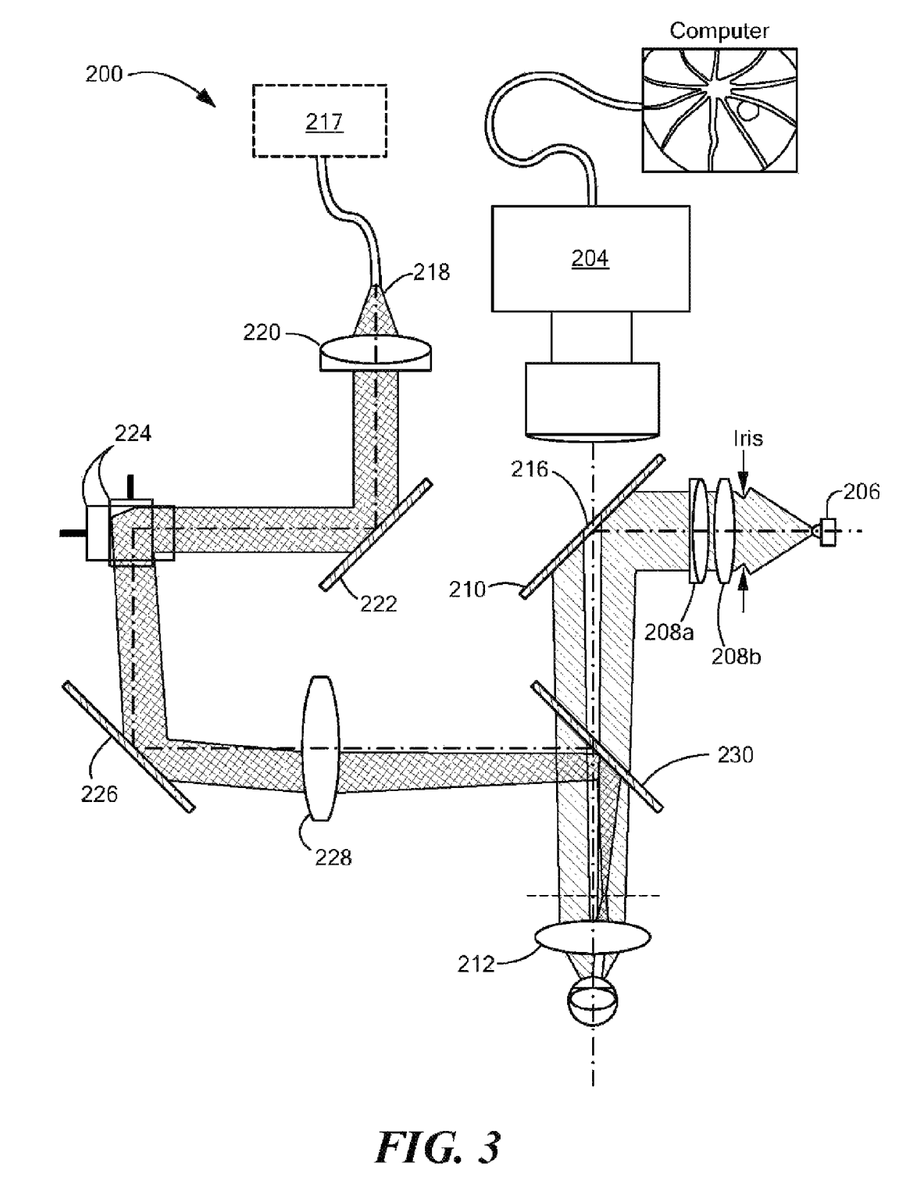
FIG. 3 is a schematic of an embodiment of the OCT imaging system.
Figure 4:
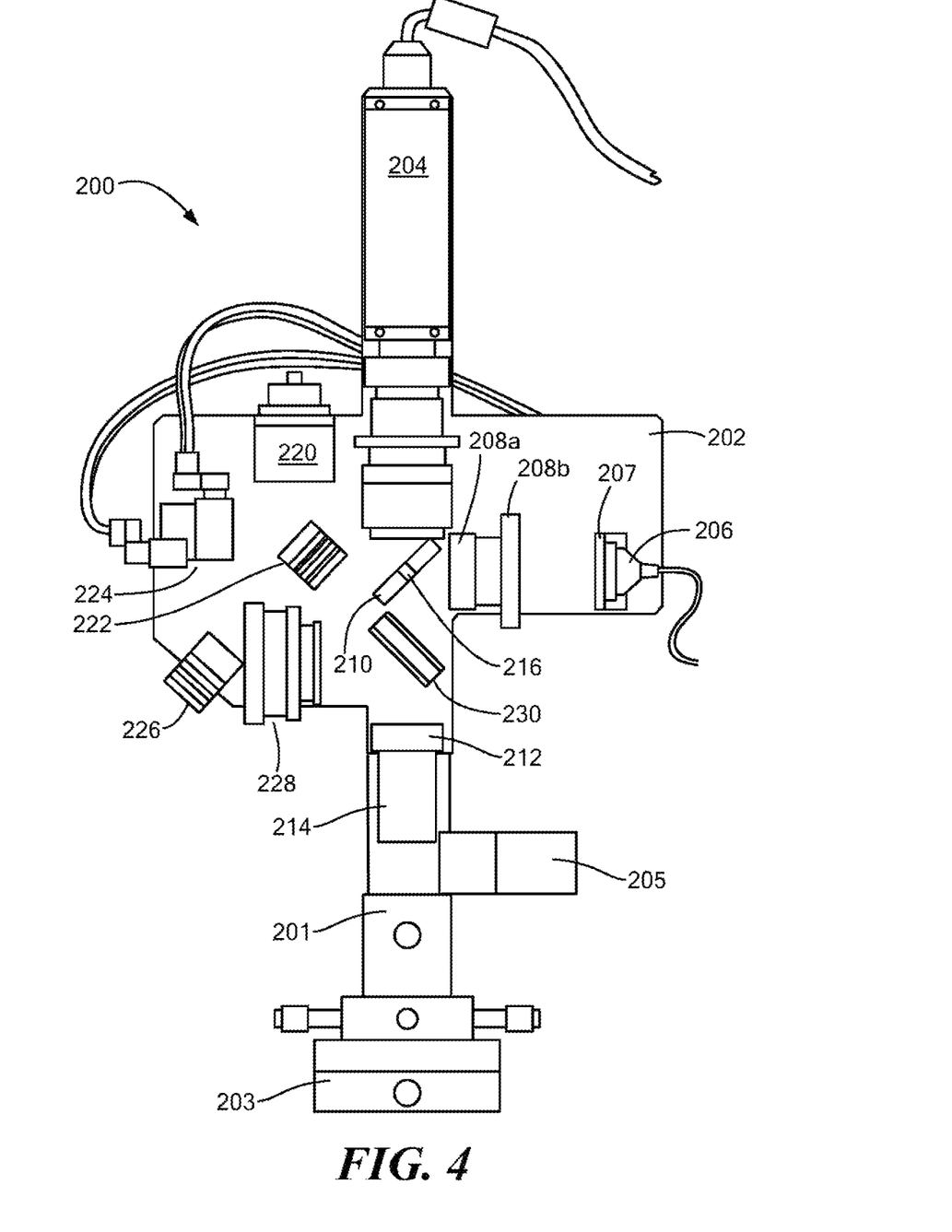
FIG. 4 is a perspective view of the imaging system of FIG. 3.

Referring now to FIG. 3 and FIG. 4, where an embodiment of the mouse fundus, retinal, or corneal imaging system referred to generally as 200 is shown. The imaging system 200 provides for a compact table-top base element 202 (seen in FIG. 4) to which the various components of the present invention may be coupled. In an embodiment, the base element 202 may be made of aluminum or other suitable material, and may be approximately two feet in height and a foot in length or any dimensions suitable for the imaging system 200 to be light-weight and portable. The base element 202 may further include a plate 203, or base, made of aluminum or other suitable material. Because the base element 202 and plate 203 define the framework of the imaging system, the two elements may be referred to together herein (i.e., "the base element 202 or plate 203") In an embodiment, the plate 203 may be approximately 27 cm² in area and may be similarly sized to the stage. The positioning stage 201 may provide for multi-axis of freedom, for example, six, and two goniometric stages. The imaging system 200 may further have an animal holder 205 that holds the anesthetized rat, mouse, or other small animal while operating the imaging system 200. The animal holder 205 may be any size or shape that may position a mouse for examination and mounted in front of the imaging system 200 on a positioning stage 201. In an embodiment, the animal holder 205 may be substantially cylindrical in shape and movably coupled to the positioning stage 201. It should be noted that FIG. 3 is a schematic of an embodiment of the OCT imaging system and, as such, shows the same elements as in FIG. 4 but without the base element 202 or plate 203.

Continuing to refer to FIGS. 3 and 4, a light source 206 may be coupled to the base element 202 or plate 203. The light source 206 may be powered by a remote power source or an internal power source. The light source may be an incandescent white light, or alternatively, be a light-emitting diode (LED). The light source 206 may emit a uniform spectrum of white light or may emit varying wavelengths of light, for example, green, yellow, red, or blue light to precisely illuminate and visualize the desired area of the fundus. A plastic lens 207 may be coupled to the light source 206 to reduce the divergence of the emitted light, and may be sized approximately 5 mm in diameter. One or more illumination lenses 208 may be coupled to the base element 202 or plate 203 proximate to the light source 206 to focus the emission from light source 206. In an embodiment, two parallel illumination lenses 208a and 208b are vertically coupled to the base element 202 to focus the emission from light source 206, creating approximately a 2.5× magnification. The illumination lenses 208a and 208b may be plastic, glass, or material to focus light and sized to be coupled to the base element 202.

The light source 206 may produce a bright uniform illumination at the aerial image plane, which is the optical conjugate of the retina. For example, the size of the aerial illumination may be approximately 10 mm In an embodiment using LEDs with a 5 mm diameter lens 207, the system of two illumination lenses 208a and 208b produce a magnification of approximately 2.5×, which corresponds to a 12.3 mm diameter illumination in the aerial image plane ($f_1$=50 mm and $f_2$=125 mm)

A reflection mirror 210 may be coupled to base element 202 or plate 203 and positioned proximal to the fundus camera 204 and to the illumination lenses 208a and 208b. The reflection mirror 210 may further be angled to reflect focused light from the light source 206. For example, as shown in FIG. 3, the reflection mirror 210 may be angled at approximately a 45 degree angle, or any angle, with respect to a longitudinal axis defined by the base element 202 to reflect focused light emitted from the light source 206. Focused light reflected from the reflection mirror 210 may then be directed toward an auxiliary lens 212, which may be coupled to the base element 202 from the fundus camera 204. The auxiliary lens 212 may be positioned proximal, for example, the mouse eye, and may generate an aerial view of the mouse retina.

In an embodiment, the auxiliary lens 212 may have a refractive power of 90 diopters (90 D) having a retinal field of view of 1.6 mm, and a resulting retinal spot size of 21.5 μm. It is further contemplated that the auxiliary lens 212 may have a refractive power depending on the desired area of the small animal eye to be imaged. For example, auxiliary lens 212 may alternatively be provided at 48, 78, or 132 D. The auxiliary lens 212 may further be coated with an anti-reflective coating to minimize any reflection off the auxiliary lens 212. A biomicroscope 214 (shown in FIG. 4) may be positioned subjacent and parallel to the auxiliary lens 212, the biomicroscope 214 being either monocular or binocular. In an embodiment using a monocular microscope 214, the objective lens generates a working distance of 116 mm.

Focused light reflected off the reflection mirror 210 and focused via the auxiliary lens 212 cooperate to create an illuminated reflection image from the mouse eye. In an embodiment using an a 90 D power auxiliary lens 212, light may be reflected off the retina of the mouse eye and refracted via the auxiliary lens 212 toward the reflection mirror 210. In an embodiment, a 90 D auxiliary lens 212 provides a 1.63 mm retinal field of view and 21 μm retinal OCT beam spot diameter. It is further contemplated that the auxiliary lens 212 may be removed from imaging system 200. In such a configuration, for example, the cornea of a rat, mouse or other small animal may be imaged.

The reflection mirror 210 may further define an aperture 216, approximately 4 mm in diameter, which may be defined proximate the center of the reflection mirror 210. The 4 mm diameter size of the aperture 216, may allow for the collection of light from all points within 1.6 mm of an optical axis defined by the mouse eye. As shown in FIG. 4, reflections originating beyond 1.6 mm may be blocked by the reflection mirror 210, and points within the 1.6 mm optical axis pass through the aperture 216 and are collected by the fundus camera 204. Because the diameter of the entrance to the mouse pupil is approximately 2 mm, it may be necessary to re-adjust the position of the mouse eye to eliminate reflections from the cornea that may occur to more precisely image the retina. The retinal image may then be passed through the aperture 216 and recorded by the fundus camera 204, providing a detailed view of the fundus.

Referring to FIG. 3, a real-time two or three-dimensional OCT image may be acquired simultaneously, or substantially simultaneously, with the fundus image discussed above. An OCT beam 218 may generated by an OCT imaging apparatus 217, attached to the base element 202, to acquire a three-dimensional retinal or corneal image as desired. The OCT imaging apparatus 217 may be, for example a time-domain system (TD-OCT) with a superluminescent diode with a center wavelength of 830 nm, a bandwidth of 45 nm, and an output of 6 mW. Alternatively, a spectral-domain OCT (SD-OCT) system may also be used. A fiber optic cable generating beam 218 in communication with the OCT imaging apparatus 217 may be coupled to the base element 202. Positioned proximal to the OCT beam 218 and coupled to the base element 202 may be a collimating lens 220. The collimating lens 220 may be fabricated to produce a larger diameter beam 218, which in turn, reduces the imaged retinal spot diameter. In an embodiment, the collimating lens 220 may be positioned subjacent to the beam 218 on the base element 202.

The beam 218 may be focused through the collimating lens 220 towards a first folding mirror 222, which may be coupled to the base element 202 or plate 203 and positioned subjacent to the collimating lens 220. The first folding mirror 222 may be angled at approximately a 45 degree angle, or any angle, with respect to the collimating lens 220. In an embodiment, the first folding mirror 222 may be oriented on the base 202 such that a longitudinal axis defined by the first folding mirror 222 may be substantially parallel to a longitudinal axis defined by the reflection mirror 210. The beam 218 may then be reflected off of the first folding mirror 222 through an X-Y scanner 224 also coupled to the base element 202 or plate 203. The X-Y scanner 224 aids in creating an OCT image of the desired retinal spot. The X-Y scanner 224 may further define an aperture, sized approximately 3 mm, to allow a portion of beam 218 to pass through on a path towards the mouse eye.

Continuing to refer to FIG. 3, the beam 218 may then be reflected off a second folding mirror 226, which may be coupled to the base element 202 or plate 203 and subjacent to the X-Y scanner 224. The second folding mirror 226 may be angled at approximately a 45 degree angle, or any angle, with respect to a longitudinal axis defined by the base element 202. In an embodiment, the second folding mirror 226 may be oriented such that a longitudinal axis defined by the second folding mirror 226 may be substantially perpendicular to the longitudinal axis defined by the first folding mirror 222. The beam 218 may then be reflected off the second folding mirror 226 towards a scanning lens 228, which is coupled to the base element 202 or plate 203. The scanning lens 228 may be oriented on the base element 202 such that a longitudinal axis defined the scanning lens 228 may be substantially perpendicular to a longitudinal axis defined by the collimating lens 220. The scanning lens 228 may have a focal length between 100-200 mm to focus the beam 218 as it approaches the mouse eye. In an embodiment, the scanning lens 228 having a focal length of 100 mm results in a retinal spot diameter of 7 μm.

Continuing to refer to FIG. 3, a hot mirror 230 may be coupled to the base element 202 or plate 203 proximate the scanning lens 228. The hot mirror 230 may be angled at approximately 45 degree angle, or any angle, with respect to a longitudinal axis defined by the base element 202 to reflect the focused beam 218 toward the mouse eye. In an embodiment, the hot mirror 230 may be oriented on the base element 202 such that a longitudinal axis defined by the hot mirror 230 maybe substantially parallel to the longitudinal axis defined by the second folding mirror 226 and substantially perpendicular to the longitudinal axis defined by the first folding mirror 222. The hot mirror 230 may have a dual function; it may allow for the passage of the visible wavelengths of light emitted by the light source 206, allowing for an unimpeded fundus image to be obtained, and also reflect the infrared wavelengths generated by the beam 218 toward the mouse eye. The focused reflected beam 218 may then image the desired retinal spot of the mouse eye and a three-dimension image is created.

It is further contemplated that a laser may be added to the above system to coagulate the retina and produce a retinal injury followed by the formation of new blood vessels, for example, choroidal neovascularization. The imaging system 200 above may be used to accurately identify a desired sport for laser treatment and then the laser may be utilized as part of a treatment protocol. Additionally, it is further contemplated that the OCT imaging apparatus 217 may be removed from the base element 202, such that the imaging system 200 operates with the fundus camera 204 and without the OCT imaging apparatus 217.

It is further contemplated that in an embodiment of the imaging system 200 using LEDs as the light source 206, flourescein angiography may be performed. In an exemplary method, a fluorescent agent may be administered systematically to a mouse in vivo. Once the fluorescein reaches the retinal circulation, fundus images may then be recorded. As contemplated by the presented invention, fluorescein may be administered intravenously to an anesthetized mouse, positioned in the animal holder 205. A blue wavelength of light may then be emitted by the light source 206. Excitation of the fluorescein with blue light emitted from the light source 206 may produce an emission with a longer wavelength light from the tissue perfused with fluorescein. The camera 204 of the present invention may then record images of the fundus to detect abnormalities in the retinal vasculature and an OCT spot may be visualized.

Figure 5:
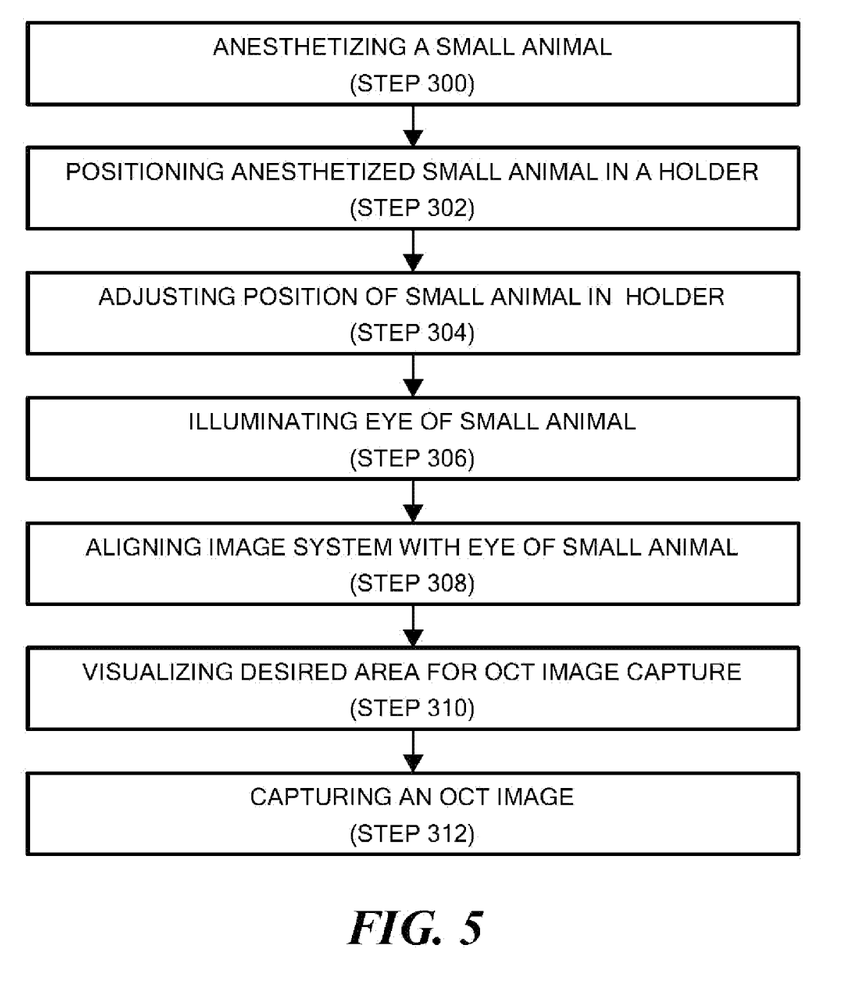
FIG. 5 is a flow chart illustrating a method of acquiring an image from the fundus of a small animal using an embodiment of the imaging apparatus of the present invention.

Referring now to FIG. 5 where a method using the imaging system 200 on mice and other small animals is shown. The method may include anesthetizing a mouse or other small animal by methods known in the art (Step 300) and placing the anesthetized mouse in animal holder 205 (Step 302), which may be any size or shape that may position a mouse for examination and mounted in front of the imaging system 200 on a positioning stage 201. The positioning stage 201 (shown in FIG. 4) may provide for multi-axes of freedom, for example, six, and two goniometric stages. For example, the positioning stage 201 may be operable such that the center of the pupil of the mouse, rat, or other small animal eye is located at the intersection of all of the goniometric axes so that the OCT spot is stationary when the mouse eye is aligned. Also, the goniometric angles may be in the range of +/−10-20 degrees. The animal holder 205 (shown in FIG. 4) may be substantially cylindrical in shape and movably coupled to the positioning stage 201.

An operator may further adjust the position of the mouse (Step 304) using a real-time video display of the mouse eye and fundus for guidance. The fundus of the eye may then be illuminated with the desired light source for the particular tissue to be imaged (Step 306) discussed in more detail below. The imaging system 200 may then be aligned with the mouse eye for image acquisition (Step 308). In an embodiment, the alignment consists of two steps, which may include coarsely adjusting the position of the mouse until a view of the retina is obtained and finely aligned the mouse eye until a clear image of the fundus fills the image screen and the OCT spot is visualized (Step 310). Once the desired spot on the fundus is visualized, an OCT image may then be acquired (Step 312). Additional spots on the fundus may be visualized and imaged depending on the desired number of images to be acquired.

The imaging system 200 may include software that saves the digital fundus image and the raw OCT image signal in exportable data files. Thickness measurements may be done manually by selecting areas in the region of interest and finding the position of the intensity peaks corresponding to the boundaries of interest. Inner retinal thickness may be measured from the intensity peak corresponding to interface of the vitreous and nerve fiber layer (NFL), to the intensity peak corresponding to the interface between the inner nuclear layer (INL) and outer plexiform layer (OPL). Outer retinal thickness may be measured from the intensity peak corresponding to the interface between the inner nuclear layer (INL) and outer plexiform layer (OPL), to the intensity peak, which corresponds to the interface between the photoreceptor layer (PL) and retinal pigment epithelium (RPE)

Figure 6:
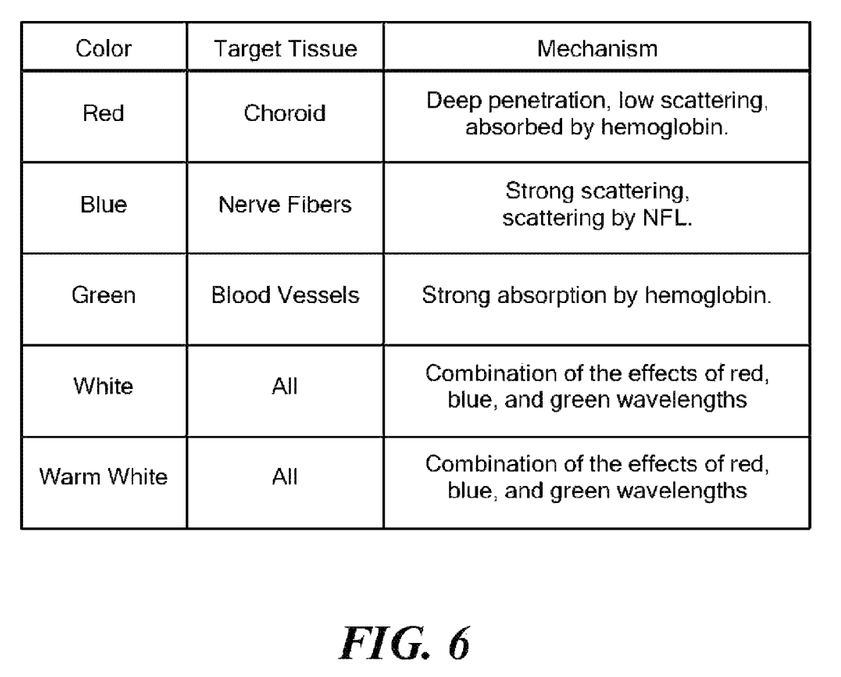
FIG. 6 is a table of the interaction of different retinal structures with different wavelengths emitted by LEDs.

For example, as shown in FIG. 6 using an LED light source 206 with a particular wavelength of light may be used to illuminate and target a specific tissue of the mouse or rat eye. Red light may be used to target choroid tissue, blue light may be used to target nerve fibers, and green light may be used to target blood vessels. Varying the wavelength along the spectrum of light may also provide a complete and detailed three-dimensional image of the fundus of the mouse or rat during simultaneous OCT image acquisition.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A small animal retinal imaging system comprising:
a base element;
a camera coupled to the base element and sized to image the eye of a small animal;
a light-emitting diode coupled to the base element;
a reflection mirror coupled to the base element proximate the camera and light-emitting diode, the reflection mirror defining an aperture having a diameter of approximately 4 mm;
an OCT imaging apparatus coupled to the base element; and
an X-Y scanner coupled to the base element in communication with the OCT imaging apparatus,
the camera and reflection minor aperture lying on a common vertical axis, the light-emitting diode and reflection mirror aperture lying on a common horizontal axis.

2. The imaging system of claim 1, further comprising a first illumination lens coupled to the base element proximal the light-emitting diode.

3. The imaging system of claim 2, further comprising a second illumination lens coupled to the base element, the second illumination lens being oriented such that a longitudinal axis defined by the second illumination lens is substantially parallel to a longitudinal axis defined by the first illumination lens.

4. The imaging system of claim 2, further comprising a first folding mirror coupled to the base element, the first folding minor being oriented such that a longitudinal axis defined by the first folding minor is substantially parallel to a longitudinal axis defined by the reflection mirror.

5. The imaging system of claim 4, further comprising a second folding mirror coupled to the base element, the second folding minor being oriented such that a longitudinal axis defined by the second folding mirror is substantially perpendicular to the longitudinal axis defined by the first folding minor.

6. The imaging system of claim 1, further comprising a hot mirror coupled to the base element, wherein the hot minor allows light emitted by the light-emitting diode to pass through the hot mirror and reflects infrared wavelengths of light generated by the OCT imaging apparatus.

7. The imaging system of claim 1, further comprising a scanning lens coupled to the base element.

8. The imaging system of claim 1, further comprising an auxiliary lens coupled to the base element.

9. The imaging system of claim 1, further comprising a collimating lens coupled to the base element proximate the OCT imaging apparatus.

10. The imaging system of claim 1, wherein the light-emitting diode emits blue light.

11. A small animal imaging system comprising:
a base element;
a camera coupled to the base element and sized to image the eye of a small animal;
an OCT imaging apparatus coupled to the base element;
a light-emitting diode coupled to the base element;
a first illumination lens coupled to the base element proximate the light-emitting diode;
a reflection mirror coupled to the base element proximate the first illumination lens, the reflection minor defining an aperture approximately at its center;
a second illumination lens coupled to the base element, the second illumination lens being oriented such that a longitudinal axis defined by the second illumination lens is substantially parallel to a longitudinal axis defined by the first illumination lens;
a first folding mirror coupled to the base element, the first folding minor being oriented such that a longitudinal axis defined by the first folding mirror is substantially parallel to a longitudinal axis defined by the reflection mirror;
a second folding mirror coupled to the base element, the second folding mirror being oriented such that a longitudinal axis defined by the second folding mirror is substantially perpendicular to the longitudinal axis defined by the first folding mirror;
a hot minor coupled to the base element, wherein the hot mirror allows light emitted by the light-emitting diode to pass through the hot minor and reflects infrared wavelengths of light generated by the OCT imaging apparatus;
a scanning lens coupled to the base element, the scanning lens being disposed between the second folding mirror and the hot mirror;
an auxiliary lens coupled to the base element;
a collimating lens coupled to the base element proximate the OCT imaging apparatus; and
an X-Y scanner coupled to the base element in communication with the OCT imaging apparatus.

* * * * *